US00RE37718E

(19) United States
(12) Reissued Patent
Blanchard et al.

(10) Patent Number: US RE37,718 E
(45) Date of Reissued Patent: May 28, 2002

(54) ION BEAM MODIFICATION OF BIOACTIVE CERAMICS TO ACCELERATE BIOINTEGRATION OF SAID CERAMICS

(75) Inventors: Cheryl Blanchard; Geoffrey Dearnaley; James Lankford, Jr., all of San Antonio, TX (US)

(73) Assignee: Southwest Research Institute, San Antonio, TX (US)

(21) Appl. No.: 08/820,813

(22) Filed: Apr. 2, 1997

Related U.S. Patent Documents

Reissue of:
(64) Patent No.: 5,496,374
Issued: Mar. 5, 1996
Appl. No.: 08/285,994
Filed: Aug. 4, 1994

(51) Int. Cl.[7] ..... A61F 2/28; B05D 3/00
(52) U.S. Cl. ..... 424/423; 427/2.26; 427/2.27; 427/523; 427/527; 427/529; 623/23.56
(58) Field of Search ..... 427/2.27, 2.26, 427/529, 527, 523; 623/16, 16.11

(56) References Cited

U.S. PATENT DOCUMENTS

| | | | | |
|---|---|---|---|---|
| 4,656,083 | A | 4/1987 | Hoffman et al. | 428/265 |
| 4,702,930 | A | 10/1987 | Heide et al. | 427/2 |
| 4,894,255 | A | 1/1990 | Page et al. | 427/38 |
| 4,944,754 | A | 7/1990 | Linkow et al. | 623/16 |
| 5,242,706 | A | 9/1993 | Cotell et al. | |
| 5,380,547 | A | 1/1995 | Higgins | 427/226 |
| 5,383,934 | A | 1/1995 | Armini et al. | 623/16 |

FOREIGN PATENT DOCUMENTS

WO 9307924 4/1993

OTHER PUBLICATIONS

T. Fujiu, et al. *Difference of bond bonding behavior among surface active glasses and sintered apatite,* Journal of Biomedical Materials Research, vol. 18, 845–859, 1984.

L.L. Hench, et al., *Reaction Kinetics of Bioactive Ceramics Part IV: Effect of Glass and Solution Composition,* Biocerramics 5, 67–74, 1992.

L.L. Hench, *Surface Reaction Kinetics and Adsorption of Biologicial Moieties: A Mechanistic Approach to Tissue. Attachment,* Univ. Of Toronto Press, 33–44.

T. Kokubo et al., *Chemical reaction of bioactive glass and glass–ceramics with a simulated body fluied,* Journal of Material Science: Materials in medicine 3, 79–83, 1992.

Tadashi Kokubo, *Surface Chemistry of Bioactive Blass–Ceramics,* Journal of Non–Crystalline Solids 120, 138–151, 1990.

M. Regina, et al., *Solution effects on the surface reactions of three bioactive glass compositions,* Journal of Biomedical Materials Research 27, 1485–1493, 1993.

Takashi Nakamura, et al., *A new glass–ceramic for bone replacement: Evaluation of its bonding to bone tissue,* Journal of Biomaterials Research, vol. 19, 685–698, 1985.

G.H. Takaoka et al., Surface Modification of Bioactive Ceramic (Artificial Bone) by Ion implantation Materials Res. Soc. Symp., Prac. vol. 252, pp. 23–28, 1992.

June Wilson, et al. *Toxicology and biocompatibility of bioglasses,* Journal of Biomedical Materials Reasearch, vol. 15, 805–817, 1981.

Larry L. Hench, *The Kinetics of Bioactive Ceramics, Bioceramics,* vol. 31, 43–53.

Larry L. Hench, *Bioceramics: From Concept to Clinic,* J. Am. Ceram. Soc., vol. 74, 1487–15120, 1991.

Tadashi Kikubo, *Bioactive Glass Ceramics: Properties and Applications,* Biomaterials, vol. 12, 155–163, 1991.

Ong, et al., Structure, solubility and bond strength of thin calcium phosphate coatings produced by ion beam sputter deposition, 6055 Biomaterials 13 (1992) No. 4, Guildford, Surrey, GB.

*Primary Examiner*—Timothy Meeks
(74) *Attorney, Agent, or Firm*—Paula D. Morris & Associates, P.C.

(57) ABSTRACT

The present invention provides for faster and stronger tissue-implant bonding by treating a ceramic implant with an ion beam to modify the surface of the ceramic. The surface modification can give the ceramic improved ion-exchange properties depending upon the particular ceramic and the type of ions used. In a preferred embodiment, a bioactive ceramic orthopaedic, dental, or soft tissue implant is bombarded with a beam of cations. When implanted in the body, the surface modification causes an increase in the release of critical ions, such as calcium or phosphorus, from the surface of the ceramic implant, and thereby accelerates implant-tissue bond formation.

36 Claims, No Drawings

ION BEAM MODIFICATION OF BIOACTIVE CERAMICS TO ACCELERATE BIOINTEGRATION OF SAID CERAMICS

Matter enclosed in heavy brackets [ ] appears in the original patent but forms no part of this reissue specification; matter printed in italics indicates the additions made by reissue.

FIELD OF THE INVENTION

The present invention relates to bioactive ceramics and to methods of treating bioactive ceramics to increase their bioactivity and improve their biointegration. In a preferred embodiment, an ion beam is used to treat orthopaedic, dental, or soft tissue implants made of ceramic oxides, particularly components made of bioactive ceramics, to accelerate implant-tissue bonding in vivo.

BACKGROUND

Bioactive materials are defined as materials which form a chemical bond with living tissue. Ceramic implant materials, such as alumina and calcium phosphate-based ceramics, may be bio-inert, biodegradable, resorbable, or bioactive depending upon their composition. True bonding between bone and man-made materials has been observed only within a limited group of ceramics, such as, the BIOGLASS® family, CERA-VITAL™, and apatite-wollastonite, all of which are based on ceramic oxide formulations.

Bioactive ceramic materials are believed to bond to bone because an oxide, or a ratio of oxides, present in the ceramic material permits a time-dependent, kinetic modification of the surface of the ceramic through an ion-exchange reaction that is triggered upon implantation into body fluids near bone or soft tissue. Upon implantation, a biologically-active calcium hydrocarbonate apatite (HA) layer forms at the surface of the ceramic. This HA layer is chemically and crystallographically equivalent to the mineral phase in bone. The equivalence between the ceramic HA layer and bone is considered to be responsible for the interfacial bonding between the ceramic implant and the bone or soft tissue. Specific to the bioactive glass-ceramic materials, the rate of release of calcium from apatite-wollastonite normally is constrained by the need to balance out-diffusion of cations and either phosphate or silicate ions in order to maintain charge neutrality.

Two problems currently exist which prevent widespread use of bioactive materials for implantation into soft or hard tissue, and for load bearing applications. These problems are (1) the extended time period required for significant hard or soft tissue-ceramic bonding following implantation, and (2) the ultimate bond strength achieved. These problems are present regardless of whether the material used for the implant is an amorphous bioactive material, such as the BIOGLASS® family, or a crystalline or semi-crystalline material, such as CERA-VITAL™ or apatite-wollastonite. However, the problems are especially critical when the material is a bioactive glass-ceramic material having a primarily crystalline structure. The glass-ceramics are stronger and better suited for load-bearing applications, but are significantly less bioactive than their glassy counterparts.

The kinetics of the ion-exchange reaction—that is, the release of critical ions (Ca, Si, Mg, Na, P, etc.) required to form a biologically-active HA layer—are believed to relate directly to both the rate of hard or soft tissue-ceramic bonding and to the strength of the resulting bond. Because phosphate ions present in body fluids can react with calcium to form HA, it is believed that the critical requirement for bonding and osseointegration of ceramics is the release of calcium.

In general, crystalline materials have stronger atomic bonds and increased stability as opposed to amorphous materials. As a result, the rate of the ion-exchange reaction for crystalline or semi-crystalline materials is significantly slower than for more amorphous materials under the same conditions. This significantly slower ion exchange reaction causes glass-ceramics to have a lower bioactivity than amorphous materials.

The rate of bonding between tissue and both crystalline and amorphous ceramics could be increased if a method could be found to increase the kinetics of this ion-exchange reaction. This would allow BIOGLASS® and the stronger bioactive glass-ceramics to become more bioactive, rendering the bioactive glass-ceramics suitable for appropriate load-bearing applications. An increase in the rate of these critical ion-exchange reactions also should result in a decreased period of patient convalescence, leading to a greater implant success rate, and an increased lifetime for ceramic implants.

SUMMARY OF THE INVENTION

The present invention provides for faster and stronger tissue-implant bonding by treating a ceramic implant with an ion beam to modify the surface of the ceramic. The surface modification can give the ceramic improved ion-exchange properties depending upon the particular ceramic and the type of ions used. In a preferred embodiment, a bioactive ceramic orthopaedic, dental, or soft tissue implant is bombarded with a beam of cations. When implanted in the body, the surface modification causes an increase in the release of critical ions, such as calcium or phosphorus, from the surface of the ceramic implant, and thereby accelerates implant-tissue bond formation. The mechanism and rate of the ion-exchange reaction, and the type and quantity of ions released by the ceramic, can be controlled by: (a) varying the depth to which the ions penetrate by varying the energy of ion bombardment or the angle of the ceramic surface related to the ion beam; (b) varying the dose (or ions per unit area) of the ion beam; and (c) varying the type and combination of ions used.

DETAILED DESCRIPTION OF THE INVENTION

The present invention describes a specific method for increasing the bioactivity of a bioactive ceramic using an ion-beam to modify the implant surface, thereby enhancing the rate of formation and strength of the tissue-implant bond. Without limiting the present invention to any particular theory or mechanism of action, it is believed that ion-beam modification, particularly using positive ions or cations, such as protons, helium ions, nitrogen ions, calcium and/or phosphorus ions, creates a non-equilibrium in the ceramic substrate which strongly favors the release of calcium for bond formation. Preferred ions for use in the present invention are calcium ions.

The present invention is directed to all ceramic implants that have been exposed to ion beams in a manner that improves the bioactivity of the ceramic. Ion-beam modification can increase the bioactivity of a ceramic surface in a number of ways, which include: (1) creating atomic disorder at the implant surface, thereby enhancing critical ion exchange reactions at the implant surface; (2) implanting cations in the implant surface, causing an increase in the release of ions and maintaining charge neutrality; and, (3) implanting calcium, which will increase the release of calcium to form the HA layer needed for bonding.

A preferred method for increasing bioactivity and improving biointegration of a ceramic implant involves the use of ion bombardment or ion implantation techniques to increase the bioactivity of substantially any bioactive ceramic material for a number of potential purposes. The extent and quality of increased bioactivity may differ depending upon the type of ceramic material and the type of ions used to bombard the material.

The present invention is useful to treat moderately-load-bearing and non-load-bearing implants which are partially or wholly made of ceramic material, and is particularly useful to treat load-bearing implants, such as orthopaedic or dental implants, which are partially or wholly made of bioactive glass-ceramics, such as BIOGLASS®, CERA-VITAL™ or apatite-wollastonite. The increased bioactivity of the treated ceramic material should enhance healing and patient convalescence. Bombarding a bioactive glass-ceramic implant with ions, as described, will increase the bioactivity of the glass-ceramic so that the glass-ceramic is suitable for use as a load-bearing implant capable of quickly forming a strong bone-implant bond.

Any standard apparatus may be used for the ion bombardment. Preferably, the apparatus should include a vacuum chamber to help keep the ceramic component clean and isolated from water molecules during the procedure. The ceramic component should be cleaned using a non-aqueous cleaning solution, preferably acetone. The component then may be placed in the vacuum chamber. Preferably, the vacuum chamber should be evacuated to a base pressure of less than about $10^{-5}$ torr. After placement in the vacuum chamber, the ceramic component may be bombarded with different types of ions, depending upon the application or type of tissue with which the component ultimately will be bonded. Also, depending upon the type of ions used and the degree of surface disorder desired, the energy of bombardment and the dose will vary.

If the bioactive component is a ceramic oxide for use in an orthopaedic, dental, or soft tissue implant, then a desirable level and type of surface disorder can be achieved by bombarding the component with positive ions, preferably with protons, helium ions, nitrogen ions, calcium ions, and/or phosphorus ions, or combinations thereof, at an energy of between about 50–1000 keV, preferably between about 200–1000 keV. Heavier biocompatible ions, such as titanium, also may be used to bombard the ceramic component; however, if heavier ions are used, then the energy level required to achieve the same level of surface disorder will increase. For example, if titanium ions are used to bombard the ceramic oxide component, the energy level must be increased to at least about 200 keV in order to achieve substantially the same volume of surface disorder as protons, helium ions, nitrogen ions, calcium, and/or phosphate ions at about 50 keV. Regardless of the ions used to bombard the ceramic, the energy level preferably should be above at least about 50 keV.

The dose or fluence required to achieve a given level of surface disorder will change with the mass of the ions used to bombard the surface. If lighter ions are used, then the required fluence increases. For example, if relatively lightweight protons or helium ions are used at an energy of about 50 keV, then the fluence required to achieve a desirable level of surface disorder should be above about $10^{16}$ ions per $cm^2$. If heavier ions are used, then the fluence required to achieve the same level of surface disorder will decrease. For example, assume that titanium ions are to be used, and that the goal is to achieve substantially the same level of surface disorder as about $10^{16}$ protons per $cm^2$ at about 50 keV. In order to achieve a similar level of surface disorder, the titanium ions should have an energy of about 200 keV and a fluence of about $2\times10^{15}$ ions per $cm^2$. Regardless of the specific energy and dosage, the power density should be maintained between about 0.1–0.5 watts/$cm^2$.

In a preferred embodiment, a glass-ceramic orthopaedic or dental implant preferably made of 45S5 BIOGLASS® is provided. The preparation of 45S5 BIOGLASS® is described in M. R. T. Filguerras, et al., Solution Effects on the Surface Reactions of Three Bioactive Glass Compositions, J. Biom. Mat. Res., 27:1485–93 (1993), incorporated herein by reference. The implant is cleaned, as described above, and bombarded with calcium ions at and energy between about 100–1000 kev, preferably about 400 kev, at a dose of about $1\times10^{13}$–$1\times10^{17}$ ions per $cm^2$, preferably about $1\times10^{13}$ ions per $cm^2$.

The increase in bioactivity of a specimen can be measured using standard in vitro test procedures well known in the art. The in vitro assay is described in L. L. Hench and G. P. Latorre, Reaction Kinetics of Bioactive Ceramics Part 4: Effect of Glass on Solution Composition, Bioceramics 5 (Kobunshi Kankokai Publishers, Kyot. 1992) 67–74, incorporated herein by reference. Briefly, right cylinder test cells, 10 mm in diameter and 3 mm thick, are suspended and soaked in simulated body fluid (SBF) in a constant temperature bath of 37° C. SBF also is well known in the art, and is described in L. L. Hench, et al. Bioceramics 5:67–74. The specimens are systematically removed after soaking for specific time periods (ranging from minutes to days depending upon the extent of measurements desired). The test cells and resulting solutions are then characterized to determine bioactivity.

The measure of bioactivity may be determined in two ways using this in vitro assay. One such procedure is Fourier transformation infrared spectroscopy (FTIR), which measures the formation of various chemical species on a material surface. FTIR is well-known in the art, and is described in L. L. Hench, et al. Bioceramics 5:67–74, which has been incorporated herein by reference. In this case, FTIR will detect the formation of crystalline hydroxylapatite (HA) on the surface of a specimen. The earlier in the in vitro test the HA is detected on the surface, the more bioactive the specimen. For example, if HA appears in the FTIR spectra of a treated specimen at around 1 hour, but does not appear in the FTIR spectra of an untreated specimen until around 6 hours, then the treated specimen has greater bioactivity than the untreated specimen.

Another method to test for increased bioactivity is to measure the ionic species in the test solutions used to soak the specimens for the in vitro tests performed after ion bombardment. The characterization technique that is used is inductively coupled plasma spectroscopy (ICP). ICP is well-known in the art, and is described in T. Kokubo, et al. J. Materials Science, Materials and Medicine 3 (1992) 79–83, incorporated herein by reference. The concentration of various ionic species in the solutions reflects the relative kinetics of the ion exchange reactions taking place, which in turn reflects the bioactivity of the substrate. For example, assume that a series of treated and untreated specimens are soaked in SBF in a constant temperature bath of 37° C. for 6 hours with tests arresting at 1 hour intervals. If ICP reveals that calcium ions enter the solution surrounding the treated specimens faster than they enter the solution surrounding the untreated specimens, then the treated specimens are more bioactive than the untreated specimens.

For purposes of the present invention, an "increase in bioactivity" means the formation of HA on the surface of a treated specimen or an increased level of calcium in the SBF surrounding the treated specimen at least five minutes, preferably at least one hour, before HA forms on the untreated specimen or a lower calcium concentration is measured in the SBF of the untreated specimen.

The foregoing in vitro analyses correlate to the results that can be expected in vivo. If FTIR and/or ICP indicate that treated specimens demonstrate increased bioactivity, then in vivo testing also should reflect that treated implants demonstrate increased bioactivity. After in vivo implantation of treated and untreated specimens, bioactivity would be measured by measuring the strength of the attachment between the implant and, e.g., the bone, after a given period of time. The strength of this attachment generally is measured by a "pushout test," similar to that described in T. Fujiu and M. Ogino, J. Biomed. Mats. Res., 18, 845 (1984), incorporated herein by reference. The more bioactive specimens would form a stronger bond in a shorter period of time.

Experiment 1

This experiment used right cylinder 45S5 BIOGLASS® test cells, 10 mm in diameter and 3 mm thick, which were specifically constructed for this experiment by one of the inventors; however, similar test cells may be obtained from U.S. Biomaterials, Alachua, Fla. The test cells were cleaned, as described above, and bombarded on both sides with the following ions under the following conditions:

TABLE I

| Species | Energy (kev) | Fluence (ions/cm$^2$) |
|---|---|---|
| Proton | 20 | $1 \times 10^{16}$ |
| Proton | 400 | $1 \times 10^{17}$ |
| Phosphorus | 200 | $1 \times 10^{13}$ |
| Phosphorus | 200 | $1 \times 10^{14}$ |
| Calcium | 400 | $1 \times 10^{13}$ |

To determine whether the surface treatments increased the bioactivity of the BIOGLASS® test cells, the previously described in vitro assay was performed and FTIR and ICP analyses were performed to compare the bioactivity of an unmodified specimen to the bioactivity of a modified specimen. The test cell specimens were suspended in SBF in covered containers made of polyethylene. The containers used in such experiments should be made of non-reactive material, and preferably should not be made of glass. The containers were maintained in a constant temperature bath at 37° C. The specimens were removed at various time intervals such as 2, 10, 60, 180, and 360 minutes and FTIR and ICP analyses were performed.

The analyses indicated that HA formed on the treated test specimens earlier than on the untreated test specimens. Similarly, elevated calcium levels appeared earlier in the SBF test solutions from treated specimens than in the SBF solutions from untreated test specimens. The most dramatic increase in bioactivity was seen in the samples treated with calcium ions. Similar tests are underway for other BIOGLASS® compositions, CERA-VITAL™, and apatite-wollastonite glass ceramics. These other ceramics are expected to yield similar results.

Knowing the ultimate use of the component, a person of skill in the art could determine the preferred: type of ions; type of ceramic; fluence; and, energy of bombardment. A person of skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A process for increasing the bioactivity and improving the biointegration of a bioactive ceramic implant comprising treating said ceramic implant with ions in a vacuum at a [dose and energy sufficient] *power density of from about 0.1 to about 0.5 watts/cm$^2$* to form a biologically-active calcium hydrocarbonate apatite layer on the surface of said ceramic implant *when said ceramic implant is placed in an actual or simulated body fluid, wherein said ions are positive ions selected from the group consisting of protons, helium ions, nitrogen ions, calcium ions, phosphorous ions and combinations thereof.*

2. [The process of claim 1] *A process for increasing the bioactivity and improving the biointegration of a bioactive ceramic implant comprising treating said ceramic implant with ions in a vacuum at a power density of from about 0.1 to about 0.5 watts/cm$^2$ to form a biologically-active calcium hydrocarbonate apatite layer on the surface of said ceramic implant when said ceramic implant is placed in actual or simulated body fluid,* wherein said increased bioactivity comprises the formation of calcium hydrocarbonate apatite on the surface of said implant at least about five minutes earlier than the formation of the calcium hydrocarbonate apatite on the surface of a untreated ceramic implant.

3. The process of claim 1 wherein said increased bioactivity comprises the formation of calcium hydrocarbonate apatite on the surface of said implant at least about one hour earlier than the formation the calcium hydrocarbonate apatite of on the surface of a untreated ceramic implant.

4. The process of claim 1 wherein said [energy and said dose are at levels which maintain the power density between about 0.1–0.5 watts/cm$^2$, and said] vacuum is less than about $10^{-5}$ torr.

5. The process of claim 2 wherein [said energy and said dose are at levels which maintain the power density between about 0.1–0.5 watts/cm$^2$, and] said vacuum is less than about $10^{-5}$ torr.

6. The process of claim 3 wherein [said energy and said dose are at levels which maintain the power density between about 0.1–0.5 watts/cm$^2$, and] said vacuum is less than about $10^{-5}$ torr.

7. The process of claim 1 wherein said *ions have an* energy [is] *of* at least about 50 keV, and said vacuum is less than about $10^{-5}$ torr.

8. The process of claim 2 wherein said *ions have an* energy [is] *of* at least about 50 keV, and said vacuum is less than about $10^{-5}$ torr.

9. The process of claim 1 wherein said ceramic implant is an amorphous or glass-ceramic oxide.

10. The process of claim 2 wherein said ceramic implant is comprised of an amorphous or glass-ceramic oxide.

11. The process of claim 3 wherein said ceramic implant is comprised of an amorphous or glass-ceramic oxide.

12. The process of claim 6 wherein said ceramic implant is comprised of an amorphous or glass-ceramic oxide.

13. The process of claim 8 wherein said ceramic implant is comprised of an amorphous or glass-ceramic oxide.

14. The process of claim 1 wherein said ions are cations;

said *ions have an* energy of bombardment [is] *of* between about 50–1000 keV; and said *ions are delivered at an* ion dose [is] *of* at least about $10^{15}$ per $cm^2$.

15. The process of claim 2 wherein said ions are cations;

said *ions have an* energy of bombardment [is] *of* between about 50–1000 keV; and said *ions are delivered at an* ion dose [is] *of* at least about $10^{15}$ per $cm^2$.

16. The process of claim 3 wherein said ions are cations;

said *ions have an* energy of bombardment [is] *of* between about 50–1000 keV; and said *ions are delivered at an* ion dose [is] *of* at least about $10^{15}$ per $cm^2$.

17. The process of claim 9 wherein said ions are cations;

said *ions have an* energy of bombardment [is] *of* between about 50–1000 keV; and said *ions are delivered at an* ion dose [is] *of* at least about $10^{15}$ per $cm^2$.

18. The process of claim 10 wherein said ions are cations;

said *ions have an* energy of bombardment [is] *of* between about 50–1000 keV; and said *ions are delivered at an* ion dose [is] *of* at least about $10^{15}$ per $cm^2$.

19. The process of claim 11 wherein said ions are cations;

said *ions have an* energy of bombardment [is] *of* between about 50–1000 keV; and said *ions are delivered at an* ion dose [is] *of* at least about $10^{15}$ per $cm^2$.

20. The process of claim 12 wherein said ions are cations;

said *ions have an* energy of bombardment [is] *of* between about 50–1000 keV; and said *ions are delivered at an* ion dose [is] *of* at least about $10^{15}$ per $cm^2$.

21. The process of claim 13 wherein said ions are cations;

said *ions have an* energy of bombardment [is] *of* between about 50–1000 keV; and said *ions are delivered at an* ion dose [is] *of* at least about $10^{15}$ per $cm^2$.

22. The process of claim 6 wherein said ceramic implant is selected from the group consisting of an orthopaedic implant and a dental implant.

23. The process of claim 10 wherein said ceramic implant is selected from the group consisting of an orthopaedic implant and a dental implant.

24. The process of claim 11 wherein said ceramic implant is selected from the group consisting of an orthopaedic implant and a dental implant.

25. The process of claim 12 wherein said ceramic implant is selected from the group consisting of an orthopaedic implant and a dental implant.

26. The process of claim 13 wherein said ceramic implant is selected from the group consisting of an orthopaedic implant and a dental implant.

27. The process of claim 21 wherein said ceramic implant is selected from the group consisting of an orthopaedic implant and a dental implant.

[28. The process of claim 14 wherein said cations are selected from the group consisting of protons, helium ions, nitrogen ions, calcium ions, phosphorus ions, and combinations thereof.]

29. The process of claim 15 wherein said cations are selected from the group consisting of protons, helium ions, nitrogen ions, calcium ions, phosphorus ions, and combinations thereof.

[30. The process of claim 16 wherein said cations are selected from the group consisting of protons, helium ions, nitrogen ions, calcium ions, phosphorus ions, and combinations thereof.]

[31. The process of claim 17 wherein said cations are selected from the group consisting of protons, helium ions, nitrogen ions, calcium ions, phosphorus ions, and combinations thereof.]

32. The process of claim 21 wherein said cations are selected from the group consisting of protons, helium ions, nitrogen ions, calcium ions, phosphorus ions, and combinations thereof.

33. The process of claim 3 wherein said *ions have an* energy [is] *of* at least about 50 keV, and said vacuum is less than about $10^{-5}$ torr.

34. A process for increasing the bioactivity of an amorphous or glass-ceramic oxide orthopaedic or dental implant, said process comprising bombarding said implant in a vacuum of less than about $10^{-5}$ torr with at least about $10^{15}$ cations per $cm^2$ at [an energy of at least about 50 keV resulting in a dose sufficient] *a power density of from about 0.1 to about 0.5 watts/cm²* to form a biologically-active calcium hydrocarbonate apatite layer on the surface of said ceramic implant*, when said ceramic implant is placed in actual or simulated body fluid, wherein said cations are selected from the group consisting of protons, helium ions, nitrogen ions, calcium ions, phosphorous ions and combinations thereof.*

35. A bioactive ceramic implant with increased bioactivity due to treatment of said implant with an ion beam in a vacuum at [an energy and a dose sufficient] *a power density of from about 0.1 to about 0.5 watts/cm²* to form a biologically-active calcium hydrocarbonate apatite layer on the surface of said ceramic implant *when said ceramic implant is placed in actual or simulated body fluid.*

36. The ceramic implant of claim 35 wherein said [treatment with an ion beam comprises bombarding said ceramic implant with ions at an energy and at a dose sufficient to maintain the] power density *is* between about 0.1–0.5 watts/$cm^2$, and said vacuum is less than about $10^{-5}$ torr.

37. The ceramic implant of claim 35 wherein said *ion beam has an* energy [is] *of* at least about 50 keV, and said vacuum is less than about $10^{-5}$ torr.

38. The process of claim 35 wherein said implant comprises an amorphous or glass-ceramic oxide and said implant is selected from the group consisting of an orthopaedic implant and a dental implant.

*39. The ceramic implant of claim 35 wherein said ions in said ion beam are cations.*

* * * * *

UNITED STATES PATENT AND TRADEMARK OFFICE

CERTIFICATE OF CORRECTION

PATENT NO. : RE 37,718 E 
DATED : May 28, 2002
INVENTOR(S) : Cheryl Blanchard, Geoffrey Dearnaley and James Lankford, Jr.

It is certified that error appears in the above-identified patent and that said Letters Patent is hereby corrected as shown below:

Column 8,
Lines 56-59, delete and insert:

-- 38. The ceramic implant of claim 35 wherein said implant comprises an amorphous or glass-ceramic oxide and said implant is selected from the group consisting of an orthopaedic implant and a dental implant. --

Signed and Sealed this

Eighth Day of October, 2002

*Attest:*

*Attesting Officer*

JAMES E. ROGAN
*Director of the United States Patent and Trademark Office*